(12) United States Patent
 Ichishima (10) Patent No.: US 8,781,799 B2
(45) Date of Patent: Jul. 15, 2014

(54) SIMULATION METHOD

(75) Inventor: Daiji Ichishima, Yokosuka (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 551 days.

(21) Appl. No.: 13/159,975

(22) Filed: Jun. 14, 2011

(65) Prior Publication Data

US 2011/0246167 A1 Oct. 6, 2011

Related U.S. Application Data

(63) Continuation of application No. PCT/JP2009/005747, filed on Oct. 29, 2009.

(30) Foreign Application Priority Data

Dec. 19, 2008 (JP) ................................. 2008-324090

(51) Int. Cl.
 *G06F 7/60* (2006.01)
(52) U.S. Cl.
 USPC ............................................................ 703/2
(58) Field of Classification Search
 CPC ... G06F 19/00; G06F 19/701; G06F 17/5018; G06F 17/5036
 USPC ............................................................ 703/2
 See application file for complete search history.

(56) References Cited

U.S. PATENT DOCUMENTS

| 8,244,504 B1* | 8/2012 | Jacobs ............................... 703/2 |
| 2005/0230239 A1* | 10/2005 | Rabitz ....................... 204/157.41 |
| 2007/0043545 A1* | 2/2007 | Yonezawa et al. ............... 703/11 |
| 2007/0061119 A1* | 3/2007 | Shimada et al. ................ 703/11 |
| 2010/0211366 A1* | 8/2010 | Ichishima et al. ................ 703/6 |

FOREIGN PATENT DOCUMENTS

JP 2006-285866 10/2006

OTHER PUBLICATIONS

Savelyev et. al ("Molecular Renormalization Group Coarse-Graining of Polymer Chains: Application to Double-Stranded DNA", Biophysical Journal vol. 96 May 2009 pp:4044-4052).*
Zou et. al ("Equation-Free Dynamic Renormalization: Self-Similarity in Multidimensional Particle System Dynamics", Princeton University, Princeton, NJ 2005, pp. 1-7).*
Kido et al ("Molecular Dynamics Simulators Workbench: COMDES", Chemical Society of Japan, 1990, pp. 1-13).*

(Continued)

*Primary Examiner* — Omar Fernandez Rivas
*Assistant Examiner* — Iftekhar Khan
(74) *Attorney, Agent, or Firm* — Squire Patton Boggs (US) LLP (57) ABSTRACT

(a) Regarding a particle system S in which the number of particles is N, the mass of each particle is m, and inter-particle interaction potential energy can be expressed by $\epsilon f$, $\alpha$ greater than 1, $\gamma$ equal to or greater than 0 and equal to or smaller than d, and $\delta$ equal to or greater than 0 are determined using a dimension number d of a space where the particle system S is arranged to obtain the number N' of renormalized particles by $N'=N/\alpha^d$, to obtain the mass m' of each of the renormalized particles by $m'=m\alpha^\delta/\alpha^\gamma$, and to obtain a renormalized interaction coefficient $\epsilon'$ by $\epsilon'=\epsilon\alpha^\gamma$. (b) Molecular dynamics calculation is carried out on a particle system S' in which the number of renormalized particles is N', the mass of each particle is the mass m' of each renormalized particle, and inter-particle interaction potential energy is expressed by $\epsilon'f$.

10 Claims, 4 Drawing Sheets

(56) References Cited

OTHER PUBLICATIONS

Chandrajit L. Bajaj("Modeling and Visualization for Dynamic Molecular Structures", The University of Texas at Austin, 2002, pp. 1-14).*

Toyoshiro Inamura et al., On Variable Scale Molecular Dynamics Simulation Based on Renormalization Technique, The Japan Society of Mechanical Engineers, No. 96/0681, Apr. 1997, pp. 202-207.

Leo P. Kadanoff, Statistical Physics Statics, Dynamics and Renormalization, Chapter 14, Real Space Renormalization Techniques, 1999, pp. 291-357.

* cited by examiner

SIMULATION METHOD

CROSS REFERENCE TO RELATED APPLICATIONS

This application is a continuation application of PCT Patent Application PCT/JP2009/005747 filed on Oct. 29, 2009, which is based on and claims priority of Japanese Patent Application JP2008-324090 filed on Dec. 19, 2008, the entire contents of which are incorporated herein by reference.

BACKGROUND OF THE INVENTION

A) Field of the Invention

The present invention relates to a simulation method and a program and in particular, to a simulation method using molecular dynamics and a program which causes a computer to execute the simulation method.

B) Description of the Related Art

Computer simulations using molecular dynamics are being carried out. In the molecular dynamics, the equation of motion of particles constituting a system serving as a simulation target is analyzed numerically. If the number of particles constituting a system serving as a simulation target increases, the amount of necessary calculation increases. With the arithmetic capacity of an existing computer, it is only possible to carry out the simulation of a system having particles of about a hundred thousand.

In order to reduce the amount of calculation necessary for the simulation, for example, as described in NPL 1 (NPL 1: Inamura, Takezawa, and Shamoto, "On Variable Scale Molecular Dynamics Simulation Based on Renormalization Technique", Transactions of the Japan Society of Mechanical Engineers (A), 1997, Vol. 63, No. 608, p. 202-207), attempts have been made to apply a renormalization technique to the molecular dynamics.

The invention relating to this application has been made by the inventors and described in PTL 1 (PTL 1: JP-A-2006-285866).

SUMMARY OF THE INVENTION

As described in "3. Numerical Calculation Method" of NPL 1, in the simulation method of NPL 1, it may be impossible to evaluate a temperature explicitly.

One object of the invention is to provide a novel simulation method using molecular dynamics and a program which causes a computer to execute the method.

Another object of the invention is to provide a simulation method capable of evaluating a temperature explicitly on the basis of a renormalization technique and a program which causes a computer to execute the method.

An aspect of the invention provides a simulation method. The simulation method includes the steps of (a) with regard to a particle system S in which the number of particles is N, the mass of each particle is m, and inter-particle interaction potential energy can be expressed by a product $\epsilon f$ of a dimensionless function f representing an inter-particle distance dependence and an interaction coefficient $\epsilon$, determining a first renormalization factor $\alpha$ greater than 1, a second renormalization factor $\gamma$ equal to or greater than 0 and equal to or smaller than d, and a third renormalization factor $\delta$ equal to or greater than 0 using a dimension number d of a space where the particle system S is arranged to obtain the number N' of renormalized particles by a conversion equation $N'=N/\alpha^d$, to obtain the mass m' of each renormalized particle by a conversion equation $m'=m\alpha^\delta/\alpha^\gamma$, and to obtain a renormalized interaction coefficient $\epsilon'$ by a conversion equation $\epsilon'=\epsilon\alpha^\gamma$, and (b) carrying out molecular dynamics calculation on a particle system S' in which the number of renormalized particles is N', the mass of each particle is the mass m' of each renormalized particle, and inter-particle interaction potential energy is expressed by a product $\epsilon'f$ of the dimensionless function f and the renormalized interaction coefficient $\epsilon'$.

Another aspect of the invention provides a simulation method. The simulation method includes the steps of (a) with regard to a particle system S in which the number of particles is N, the mass of each particle is m, and inter-particle interaction potential energy can be expressed by a product $\epsilon f$ of a dimensionless function f representing an inter-particle distance dependence and an interaction coefficient $\epsilon$, determining a first renormalization factor $\alpha$ greater than 1 and a third renormalization factor $\delta$ equal to or greater than 0 using a dimension number d of a space where the particle system S is arranged to obtain the number N' of renormalized particles by conversion equation $N'=N/\alpha^d$ and to obtain the mass m' of each renormalized particle by a conversion equation $m'=m\alpha^\delta$, and (b) carrying out molecular dynamics calculation on a particle system S' in which the number of renormalized particles is N', the mass of each particle is the mass m' of each renormalized particle, and inter-particle interaction potential energy is expressed by the product $\epsilon f$ of the dimensionless function f and the interaction coefficient $\epsilon$.

Yet another aspect of the invention provides a simulation method. The simulation method includes the steps of (d) with regard to a particle system S in which the number of particles is N, the mass of each particle is m, and inter-particle interaction potential energy can be expressed by a product $\epsilon f$ of a dimensionless function f representing inter-particle distance dependence and an interaction coefficient $\epsilon$, and an XYZ orthogonal coordinate system in a space where the particle system S is arranged, on the basis of a renormalization factor $\alpha_X$ in an X direction, a renormalization factor $\alpha_Y$ in a Y direction, and a renormalization factor $\alpha_Z$ in a Z direction greater than 1, obtaining the number N' of renormalized particles by a conversion equation $N'=N/(\alpha_X\alpha_Y\alpha_Z)$, and further determining a renormalization factor $\delta$ equal to or greater than 0 to obtain the mass $m_X'$ of each renormalized particle regarding the X direction by a conversion equation $m_X'=m\alpha_X^\delta$, to obtain the mass $m_Y'$ of each renormalized particle regarding the Y direction by a conversion equation $m_Y'=m\alpha_Y^\delta$, and to obtain the mass $m_Z'$ of each renormalized particle regarding the Z direction by a conversion equation $m_Z'=m\alpha_Z^\delta$, and (e) carrying out molecular dynamics calculation on a particle system S', in which the number of renormalized particles is N', the mass of each particle is the mass m' of each renormalized particle, and inter-particle interaction potential energy is expressed by the product $\epsilon f$ of the dimensionless function f and the interaction coefficient $\epsilon$, using the mass $m_X'$ of each renormalized particle regarding the X direction for an equation of motion in the X direction, the mass $m_Y'$ of each renormalized particle regarding the Y direction for an equation of motion in the Y direction, and the mass $m_Z'$ of each renormalized particle regarding the Z direction for an equation of motion in the Z direction.

The number N' of renormalized particles is smaller than the number N of particles. For this reason, molecular dynamics calculation can be carried out on the particle system S' with a small amount of calculation compared to a case where molecular dynamics calculation is carried out on the particle system S.

The renormalization factor $\delta$ equal to or greater than 0 is arbitrarily determined and calculation is carried out, thus it is possible to carry out a simulation flexibly.

DESCRIPTION OF THE PREFERRED EMBODIMENTS

First, molecular dynamics (MD) will be simply described. A particle system in which the number of particles (for example, atoms) is N, and the Hamiltonian H is expressed by the following equation is taken into consideration.

$$H = \sum_{j=1}^{N} \left[ \frac{p_j^2}{2m} + \sum_{i=j+1}^{N} \phi(q_i - q_j) \right] \quad (1)$$

Here, the mass of each particle is m, the momentum vector of a particle j is $p_j$, the position vector (position coordinate) of the particle j is $q_j$, and inter-particle interaction potential energy is $\phi$.

If Hamiltonian H is substituted in a Hamiltonian canonical equation, the following equations of motion for each particle are obtained.

$$\frac{dp_j}{dt} = -\sum_{i \neq j}^{N-1} \frac{\partial \phi(q_i - q_j)}{\partial q_j} \quad (j = 1, \ldots, N) \quad (2)$$

$$\frac{dq_j}{dt} = \frac{p_j}{m} = v_j \quad (j = 1, \ldots, N) \quad (3)$$

In the equation (3), $v_j$ is the velocity vector of the particle j. In molecular dynamics, for each particle constituting a particle system, an equation of motion expressed by the equations (2) and (3) is numerically integrated and solved, obtaining the momentum vector (or velocity vector) and the position vector of each particle at each time. With the numerical integration, in many cases, a Verlet method is used. The Verlet method is described in, for example, J. M. Thijssen, "Computational Physics", Cambridge University Press (1999), p. 175. Various physical quantities of a system can be calculated on the basis of the position and speed of each particle obtained by molecular dynamics calculation.

Next, molecular dynamics (this is called renormalization group molecular dynamics) using a renormalization group method will be conceptually described.

In renormalization group molecular dynamics, a desired system S in which the physical quantities will be obtained is associated with a system (this is called a renormalized system S') having a smaller number of particles than the system S. Next, molecular dynamics calculation is carried out on the renormalized system S'. The calculation result on the renormalized system S' is associated with the desired system S. Thus, it becomes possible to calculate the physical quantities of the desired system S with a small amount of calculation compared to a case where molecular dynamics calculation is carried out directly on the desired system S. A conversion rule which associates the physical quantity (for example, number of particles, the mass of each particle, and the like) in the desired system S with the physical quantities in the renormalized system S' is called a scale conversion rule.

Next, the scale conversion rule which has been found by the inventors will be described. It is assumed that the desired particle system S in which the physical quantities will be calculated has N particles. It is assumed that the entire Hamiltonian H of the particle system S is expressed as shown in the equation (1).

The Hamiltonian $H_j$ of a certain particle j is expressed as follows.

$$H_j = \frac{p_j^2}{2m} + \sum_{i=j+1}^{N} \phi(q_i - q_j) \quad (4)$$

For discussion on renormalization, interaction potential energy $\phi$ is expressed as follows by a product of a function f which represents inter-particle distance dependence and is dimensionless and a coefficient $\epsilon$ (this is called an interaction coefficient $\epsilon$) which represents interaction intensity and has a dimension of energy.

$$\phi(q_i - q_j) = \epsilon f\left(\frac{q_i - q_j}{\sigma}\right) \quad (5)$$

For example, with regard to an inactive atom, the following interaction potential is used.

$$\phi(r) = \epsilon \left[ \left(\frac{\sigma}{r}\right)^{12} - \left(\frac{\sigma}{r}\right)^{6} \right] \quad (6)$$

Here, r is an inter-atom distance. The interaction coefficient $\epsilon$ and the constant $\sigma$ have values corresponding to the type of atom.

Next, a method of deriving a renormalized Hamiltonian H' from the Hamiltonian H will be described. As described below in detail, the renormalized Hamiltonian H' is obtained by executing a part of integration in a partition function $Z(\beta)$ for the particle system S, coarsely graining the Hamiltonian, and subsequently rescaling an integration variable.

For the particle system S, the partition function $Z(\beta)$ of a canonical ensemble with a constant number of particles is expressed as follows.

$$Z(\beta) = \int d\Gamma_N \exp(-\beta H(p,q)) \quad (7)$$

Here, the coefficient $\beta$ is defined as $\beta = 1/(k_B T)$ on the basis of the temperature T of the system and the Boltzmann constant $k_B$. $d\Gamma_N$ is a volume element in a phase space and is specifically expressed as follows.

$$d\Gamma_N = \frac{1}{W_N} \prod_{j=1}^{N} dp_j dq_j = \frac{1}{W_N} D_p^N D_q^N \quad (8)$$

Here, $W_N$ is $N!h^{3N}$ (where h is the Planck constant). $D_p^N$ and $D_q^N$ are respectively defined as follows.

$$D_p^N = \prod_{j=1}^{N} dp_j$$

$$D_q^N = \prod_{j=1}^{N} dq_j$$

It is difficult to discuss renormalization of a potential other than a harmonic oscillator. Accordingly, it is considered that an interaction potential having a saddle point is divided into three regions. Since the inter-particle distances $r \to \infty$ and $r \to 0$ are fixed points, the potential is invariable at the time of renormalization conversion. Thus, it is assumed that renormalization conversion near the saddle point is established for all the inter-particle distances r. Around the saddle point is subjected to Taylor expansion, and fluctuations up to a second-order fluctuation remain. If the position of the saddle point is $r_0$, and the relative displacement is $\delta u$, the first-order term of $\delta u$ is cleared, and the following equation is obtained.

$$\phi(r_0 + \delta u) = \phi(r_0) + \frac{1}{2}\left[\frac{\partial^2 \phi(r)}{\partial r^2}\right]_{r=r_0} \delta u^2 \quad (9)$$

Thus, for the particle j, the Hamiltonian which describes near the saddle point is a follows.

$$H_j = \frac{p_j^2}{2m} + \sum_{i=j+1}^{N} \left[\frac{1}{2}\phi''(r_0)|u_i - u_j|^2 + \phi(r_0)\right] \quad (10)$$

Here, $u_i$ and $u_j$ respectively represent the displacement from the saddle points of particles i and j. $\phi''$ is a second order differential for the inter-particle distance r.

Next, coarse graining of an inter-particle interaction portion of the partition function $Z(\beta)$ will be described. Consideration is first made on coarse graining in a particle system arranged on a one-dimensional chain, and is expanded to a particle system arranged on a simple cubic lattice.

Figure 1A:
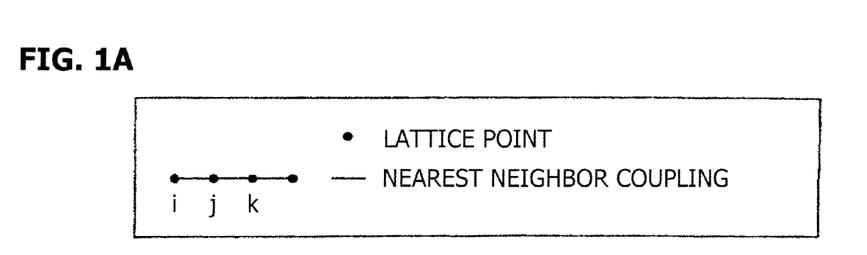
FIG. 1A is a diagram illustrating a method of deriving a scale conversion rule.

As shown in FIG. 1A, at the lattice points on a one-dimensional chain, particles i and j are arranged to be nearest neighbor, and particles j and k are arranged to be nearest neighbor. The particle j is arranged between the particles i and k. The interaction (nearest neighbor coupling) between nearest neighbor particles is indicated by a solid line. It is considered that the particle j is erased, and coarse graining is carried out. If the interaction in which the particle j involves is written, and the displacement $u_j$ of the particle j between the particles i and k is integrated, for the interaction potential $\phi'(q_i - q_k)$ of the particles and k after the influence of the particle j is renormalized, the following equation is obtained.

$$\exp(-\beta\phi'(q_i - q_k)) = \int_{-\infty}^{\infty} du_j \exp\left[-\beta\phi''(r_0)\left\{\frac{(u_i - u_j)^2}{2} + \frac{(u_j - u_k)^2}{2} + 2\frac{\phi(r_0)}{\phi''(r_0)}\right\}\right] \quad (11)$$

$$= \int_{-\infty}^{\infty} du_j \exp\left[-\beta\phi''(r_0)\left\{\frac{(u_i^2 + u_k^2)}{2} + u_j^2 - u_j \cdot (u_j + u_k) + 2\frac{\phi(r_0)}{\phi''(r_0)}\right\}\right]$$

$$= \left(\frac{2\pi}{\beta\phi''(r_0)}\right)^{\frac{3}{2}} \exp\left[-2\beta\phi''(r_0)\left\{\frac{(u_i - u_k)^2}{4.2} + \frac{\phi(r_0)}{\phi''(r_0)}\right\}\right]$$

With the coarse graining, a lattice constant becomes $\alpha$ (=2) times, in the same form as the original potential function on the basis of a variable u' subjected to scale conversion by the equation $u' = u/\alpha$. That is, the following similarity rule is obtained.

$$\exp(-\beta\phi'(q_i - q_k)) = \left(\frac{2\pi}{\beta\phi''(r_0)}\right)^{\frac{3}{2}} \exp\left[-\alpha\beta\phi''(r_0)\left\{\frac{(u_i' - u_k')^2}{2} + \frac{\phi(r_0)}{\phi''(r_0)}\right\}\right] \quad (12)$$

$$= \left(\frac{2\pi}{\beta\phi''(r_0)}\right)^{\frac{3}{2}} \exp\left(-\alpha\beta\varepsilon f\left(\frac{q_i/\alpha - q_k/\alpha}{\sigma}\right)\right)$$

However, in moving to the second row of the equation (12), it was confirmed that the same renormalization conversion is also established other than near the saddle point, $\alpha$ is called a first renormalization factor.

Coarse graining in a d-dimensional simple cubic lattice can be realized by a potential moving method. Potential Moving is explained in, for example, Leo P. Kadanoff, "STATISTICAL PHYSICS, Statics, Dynamics and Renormalization", World Scientific (1999), Chap. 14.

Figure 1B:
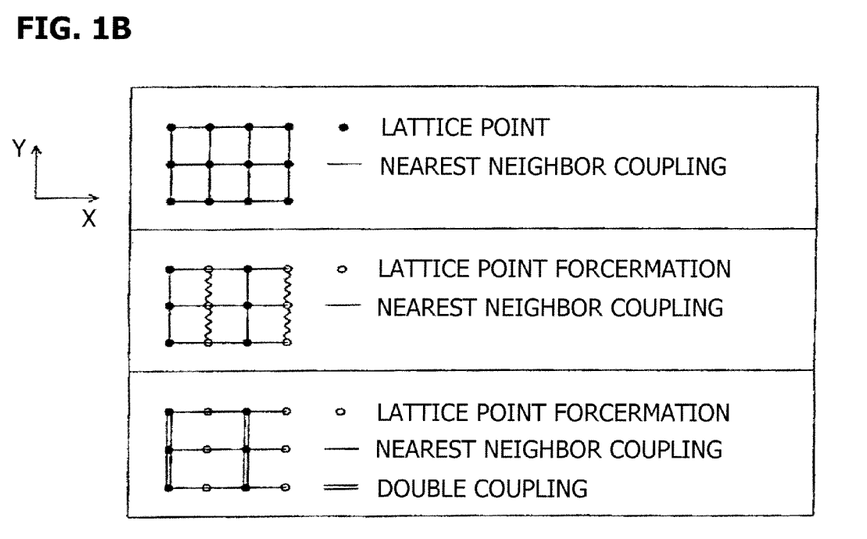
FIG. 1B is a diagram illustrating a method of deriving a scale conversion rule.

A way of thinking potential moving will be described with reference to FIG. 1B. In potential moving, a multidimensional lattice is resolved to a one-dimensional chain. FIG. 1B shows an example of a two-dimensional lattice.

As shown in the upper part of FIG. 1B, particles are arranged on the lattice points of a two-dimensional cubic lattice. The interaction (nearest neighbor interaction) between nearest neighbor particles is indicated by a solid line. The direction parallel to the side of the lattice is referred to as the X direction, and the direction perpendicular to the X direction is referred to as the Y direction.

As shown in the middle part of FIG. 1B, it is considered that, for the particles arranged in the X direction, every other particle is integrated, i.e., a particle on a lattice point (lattice point forcemation) indicated by an unshaded circle is integrated. A particle to be integrated (erased) is called an integrated particle. The nearest neighbor interaction between integrated particles is indicated by a broken line. If there is no nearest neighbor interaction between integrated particles, the integrated particles are regarded as a one-dimensional chain extending in the X direction.

In potential moving, as shown in the lower part of FIG. 1B, the nearest neighbor interaction between the integrated particles is distributed to the particles arranged on both side of an integrated particle in the X direction. The inter-particle interaction (double coupling) to which the distributed interaction is added is indicated by a double line. The interaction indicated by the double line has intensity two times greater than the original nearest neighbor interaction. In this way, for the integrated particles, a two-dimensional lattice can be converted to a one-dimensional chain. Thus, for the integrated particles, a method of coarse graining of the above-described one-dimensional chain can be executed. For example, in the case of a three-dimensional lattice, the same procedure as described above is repeated in the Y and Z directions. In this way, coarse graining in a multidimensional lattice is executed.

If the potential moving method is used, for coarse graining of an interaction portion of the partition function $Z(\beta)$ in the d-dimensional simple cubic lattice, the following result is derived.

$$\int D_q^N \exp\left(-\beta \sum_{j=1}^{N} \sum_{i=j+1}^{N} \phi(q_i - q_j)\right) \propto \qquad (13)$$

$$\int D_q^{N'} \exp\left(-\beta \alpha^d \sum_{j=1}^{N} \sum_{i=j+1}^{N} \varepsilon f\left(\frac{q_i/\alpha - q_j/\alpha}{\sigma}\right)\right)$$

Here, the number $N'$ of renormalized particles and the first renormalization factor $\alpha$ are expressed by the following equations.

$$N' = N/\alpha^d$$

$$\alpha = 2^n$$

n is a positive integer and represents the number of times of coarse graining.

Next, coarse graining of a kinetic energy portion of the partition function $Z(\beta)$ will be described. First, consideration is made in a one-dimensional chain. Particles $j-1$ and $j$ which form a pair of nearest neighbor particles are coarsely grained to one particle. The way of thinking of the block spin method of Kadanoff is applied to a momentum, and the momentum $g_j$ of the coarsely grained particle having the particles $j$ and $j-1$ is defined as follows.

$$g_j = (p_j + p_{j-1})/2$$

A weighting function $T\{P,p\}$ is defined as follows.

$$T\{P, p\} = \prod_{j=1}^{\frac{N}{2}} \delta(P_j - g_j)$$

Here, $\delta$ is a $\delta$-function of Dirac. Undoubtedly, the following condition is satisfied.

$$\int_{-\infty}^{\infty} \prod_{j=1}^{\frac{N}{2}} dP_j T\{P, p\} = 1$$

Under this condition, the weighting function $T\{P,p\}$ can be inserted into the kinetic energy portion $Z_p$ of the partition function, thus the following equation is obtained.

$$Z_p = \int D_P^{\frac{N}{2}} \int D_p^N T\{P, p\} \exp\left(-\beta \sum_i \frac{p_i^2}{2m}\right) \qquad (14)$$

-continued $$= \int D_P^{\frac{N}{2}} \int D_p^N \exp\left(-\beta \sum_i^N \frac{p_i^2}{2m}\right)$$

$$\prod_{j=1}^{\frac{N}{2}} \delta\left(P_j - \frac{p_{2j} + p_{2j-1}}{2}\right)$$

With the integral representation of the $\delta$-function, the kinetic energy portion $Z_p$ of the partition function is expressed as follows.

$$Z_p = \left(\frac{1}{2\pi}\right)^{\frac{N}{2}} \int_{\infty}^{-\infty} D_P^{\frac{N}{2}} \int_{\infty}^{-\infty} D_t^{\frac{N}{2}} \int D_p^N \qquad (15)$$

$$\exp\left[-\beta \sum_i^N \frac{p_i^2}{2m} + i \sum_j^{\frac{N}{2}} t_j \cdot \left(P_j - \frac{p_{2j} + p_{2j-1}}{2}\right)\right]$$

$$= \left(\frac{1}{2\pi}\right)^{\frac{N}{2}} \int_{\infty}^{-\infty} D_P^{\frac{N}{2}} \int D_t^{\frac{N}{2}} \exp\left(-i \sum_i^{\frac{N}{2}} P_j \cdot t_j\right) \times$$

$$\int_{\infty}^{-\infty} D_p^N \exp\left[-\sum_j^{\frac{N}{2}} \left(\frac{\beta}{2m} p_{2j}^2 + \frac{i}{2} t_j \cdot p_{2j}\right)\right]$$

$$\exp\left[-\sum_j^{\frac{N}{2}} \left(\frac{\beta}{2m} p_{2j-1}^2 + \frac{i}{2} t_j \cdot p_{2j-1}\right)\right]$$

This integration can be easily executed if the following formula is used.

$$\int D_t \exp\left[\frac{1}{2}\langle t, Kt\rangle + \langle p, t\rangle\right] = \frac{1}{\sqrt{\det\left(\frac{K}{2\pi}\right)}} \exp\frac{1}{2}\langle p, K^{-1}p\rangle$$

Here, $\langle A, B \rangle$ represents the inner product of vectors $A$ and $B$. If this formula is used, the kinetic energy portion $Z_p$ of the partition function can be expressed as follows.

$$Z_p = \left(\frac{1}{2\pi}\right)^{\frac{3N}{2}} \left(\frac{2\pi m}{\beta}\right)^{\frac{3N}{2}} \int D_P^{\frac{N}{2}} \int_{\infty}^{-\infty} D_t^{\frac{N}{2}} \qquad (16)$$

$$\exp\left(-\frac{1}{2} \sum_j^{\frac{N}{2}} t_j \cdot \left(\frac{m}{\beta}\right) t_j + \sum_j^{\frac{N}{2}} it_j \cdot P_j\right)$$

$$= \left(\frac{2\pi m}{\beta}\right)^{\frac{3N}{4}} \int D_P^{\frac{N}{2}} \exp\left(-2\beta \sum_{j=1}^{\frac{N}{2}} \frac{P_j^2}{2m}\right)$$

With this coarse graining, the kinetic energy becomes $\alpha$ (=2) times. If the entire kinetic energy of two particles is divided into the kinetic energy of the center of gravity and the kinetic energy of the relative momentum, and the relative momentum is integrated, the same result is obtained.

Next, consideration is made as to coarse graining in a d-dimensional simple cubic lattice. First, in the case of coarse graining in the direction of the crystal axis a, the kinetic energy $E_{kin}$ of a particle becomes $\alpha$ times. Successively, in the case of coarse graining in the b-axis direction, the kinetic energy $E_{kin}\alpha$ of a particle becomes $\alpha$ times as large as $E_{kin}\alpha$, that is, $E_{kin}\alpha^2$. Thus, in the d-dimensional lattice, the kinetic energy becomes $E_{kin}\alpha^d$, and the following relation expression is obtained.

$$\int D_p^N \exp\left(-\beta \sum_{j=1}^{N} \frac{p_j^2}{2m}\right) \propto \int D_p^{N'} \exp\left(-\beta\alpha^d \sum_{j=1}^{N'} \frac{p_j^2}{2m}\right) \quad (17)$$

In the case of coarse graining n times, it is obvious that $\alpha=2^n$.

From the above discussion, the partition function $Z(\beta)$ of the entire Hamiltonian subjected to coarse graining can be expressed, excluding a coefficient which does not affect the result.

$$Z(\beta) = \int d\Gamma_{N'} \exp\left[-\beta\alpha^d \sum_{j=1}^{N'} \left\{\frac{p_j^2}{2m} + \varepsilon \sum_{i=j+1}^{N'} f\left(\frac{q_i/\alpha - q_j/\alpha}{\sigma}\right)\right\}\right] \quad (18)$$

Next, in order to set the Hamiltonian of the same form for the system subjected to coarse graining, "renormalized" variables are introduced. As described below, a renormalized position vector q', a renormalized momentum vector p', a renormalized mass m', a renormalized interaction coefficient $\epsilon'$, and a renormalized coefficient $\beta'$ are defined. Scale conversion is done such that the form of the Hamiltonian is invariable.

$q' = q/\alpha$ $p' = p\alpha^{\delta/2}$ $m' = m\alpha^{\delta-\gamma}$ $\epsilon' = \epsilon\alpha^\gamma$ $\beta' = \beta\alpha^{d-\gamma}$ Here, $\gamma$ is equal to or greater than 0 and equal to or smaller than d. $\gamma$ is called a second renormalization factor. $\delta$ has a value equal to or greater than 0. $\delta$ is called a third renormalization factor.

The renormalized variables are defined in the above-described manner, such that the renormalized Hamiltonian H' of the same form as the Hamiltonian H is obtained. The renormalized Hamiltonian H' is expressed as follows.

$$H' = \sum_{j=1}^{N'} \left\{\frac{p_j'^2}{2m'} + \varepsilon' \sum_{i=j+1}^{N'} f\left(\frac{q_i' - q_j'}{\sigma}\right)\right\} \quad (19)$$

From the equation (18), the partition function is as follows.

$Z(\beta) = \int d\Gamma_{N'} \exp(-\beta' H'(p',q';m',\epsilon'))$      (20)

Here, a volume element of a phase space is as follows, excluding a coefficient which does not affect the result.

$$d\Gamma_{N'} = \frac{1}{W_{N'}} \prod_{j=1}^{N'} dp_j' dq_j' \quad (21)$$

In the system (renormalized particle system S') which is described by the renormalized Hamiltonian H', the equations of motion are given from the following canonical equations.

$$\frac{dp_i'}{dt'} = \frac{\partial H'}{\partial q_i'} \quad (i=1,\ldots,N') \quad (22)$$

$$\frac{dq_i'}{dt'} = \frac{\partial H'}{\partial p_i'} \quad (i=1,\ldots,N') \quad (23)$$

The equations of motion become the following equations.

$$\frac{dp_i'}{dt'} = -\varepsilon' \sum_{j\neq i}^{N'} \frac{\partial}{\partial q_i'} f\left(\frac{q_i' - q_j'}{\sigma}\right) \quad (i=1,\ldots,N) \quad (24)$$

$$\frac{dq_i'}{dt'} = \frac{p_i'}{m'} = v_i' \quad (i=1,\ldots,N') \quad (25)$$

Here, the following equation is established such that a renormalized time t' matches with the renormalized variables q', p', m', and $\epsilon'$.

$t' = q'/v't/\alpha^{(1+\gamma-\delta/2)}$

Molecular dynamics calculation can be carried out on the renormalized particle system S on the basis of the equations (24) and (25) of motion.

The above consideration is concluded. The particle system S and the renormalized particle system S' are associated with each other by a scale conversion rule expressed by the following conversion equations.

The number N of particles of the particle system S and the number N' of renormalized particles of the renormalized particle system S' are associated with each other by the following conversion equation.

$N' = N/\alpha^d$      (conversion equation N)

The position vector q of a certain particle of the particle system S and the position vector q' of a certain particle of the renormalized particle system S' are associated with each other by the following conversion equation.

$q' = q/\alpha$      (conversion equation q)

The momentum vector p of a certain particle of the particle system S and the momentum vector p' of a certain particle of the renormalized particle system S' are associated with each other by the following conversion equation.

$p' = p\alpha^{\delta/2}$      (conversion equation p)

The mass m of each particle of the particle system S and the mass m' of each particle of the renormalized particle system S are associated with each other by the following conversion equation.

$m' = m\alpha^{\delta-\gamma}$      (conversion equation m)

The interaction coefficient $\epsilon$ in the particle system S and the interaction coefficient $\epsilon'$ in the renormalized particle system S' are associated with each other by the following conversion equation.

$$\epsilon' = \epsilon \alpha^\gamma \qquad \text{(conversion equation } \epsilon\text{)}$$

A time scale t (a certain time interval t in molecular dynamics calculation which is supposed to be carried out on the particle system S) when the equation of motion is resolved for the particle system S and a time scale t' (a certain time interval t' in molecular dynamics calculation which is carried out on the renormalized particle system S') when the equation of motion is resolved for the renormalized particle system S' are associated with each other by the following conversion equation.

$$t' = t/\alpha^{(1+\gamma-\delta/2)} \qquad \text{(conversion equation t)}$$

The velocity vector v of a certain particle of the particle system S and the velocity vector v' of a certain particle of the renormalized particle system S' are associated with each other by the following conversion equation because the velocity vector v is expressed by v=p/m.

$$v' = v\alpha^{(\gamma-\delta/2)} \qquad \text{(conversion equation v)}$$

Here, the dimension number of a space where the particle system S is arranged is d. The first renormalization factor $\alpha$ is $2^n$ (where n is a positive integer), and the second renormalization factor $\gamma$ is equal to or greater than 0 and equal to or smaller than d. The third renormalization factor $\delta$ is equal to or greater than 0.

When the value of the second renormalization factor $\gamma$ is large, for example, equal to d, a very large renormalized interaction coefficient $\epsilon'$ and a small renormalized mass m' appear in numerical calculation. In numerical calculation, it is preferable that the second renormalization factor $\gamma$ is set to 0. At this time, if the third renormalization factor $\delta$ is also set to 0, only the time t is converted, and the MD of the related art can be used.

For example, when $\delta=2$, with regard to a spring-mass system of a one-dimensional chain having a mass m and a spring constant s, the dispersion relationship is obtained as follows from the renormalized Hamiltonian.

$$\omega = \pm \left(\frac{4s}{m}\right)^{\frac{1}{2}} \frac{1}{\alpha} \sin\left(\frac{k\alpha a}{2}\right) \qquad (26)$$

Here, an angular velocity is $\omega$, and a wave number is k. An inter-atom distance in an equilibrium state is a. The second renormalization factor $\gamma$ was set to 0. The equation (26) becomes as follows in the limit of a long wavelength, and has no relation to the first renormalization factor $\alpha$.

$$\omega = \pm \left(\frac{sa^2}{m}\right)^{\frac{1}{2}} k \qquad (27)$$

Next, an example of a computer simulation by renormalization group molecular dynamics will be described.

First, a simulation in which heat flows in aluminum to raise the temperature, and a melting point and latent heat are calculated will be described. In a first simulation, for comparison, molecular dynamics calculation (with no renormalization applied) of the related art was carried out on a system having 16000 aluminum atoms. The aluminum atoms are arranged in a three-dimensional space, and the dimension number d is 3.

In second and third simulations, molecular dynamics calculation was carried out on a system renormalized from the system corresponding to the first simulation. The first renormalization factor $\alpha$ is determined to be 2 in the second simulation and $2^2$ (=4) in the third simulation. From the (conversion equation N), the number of particles of the system in the second simulation becomes 2000, and the number of particles of the system in the third simulation becomes 250. The second renormalization factor $\gamma$ was determined to be 0. The third renormalization factor $\delta$ was determined to be 2. The related art method (first simulation) corresponds to a case where the first renormalization factor $\alpha$ is set to 1.

In the first simulation, the Morse potential was used as an inter-atom potential (that is, an inter-particle potential in the original system). This potential is expressed as follows.

$$\phi(r) = \epsilon \{e^{-2A(r-r_0)} - 2e^{-A(r-r_0)}\} \qquad (28)$$

Here, the interaction coefficient $\epsilon$ is $1.92 \times 10^{-20}$ [J], the constant A is $2.35 \times 10^{10}$ [m$^{-1}$], and the constant $r_0$ is $2.86 \times 10^{-10}$ [m]. The inter-particle distance is r.

In the second and third simulations, the same form as in the equation (28) is used as the inter-particle potential (that is, the inter-particle potential in the renormalized system). The renormalized interaction coefficient in each of the second and third simulations is found by the (conversion equation $\epsilon$). Since the second renormalization factor $\gamma$ is 0, the interaction coefficient in each of the second and third simulations is the same as the interaction coefficient $\epsilon$ in the first simulation. The constant $r_0$ and the constant A are the same as those in the first simulation.

The mass of each aluminum atom in the first simulation (that is, the mass of each particle in the original system) is $4.48 \times 10^{-26}$ [kg]. The renormalized mass of each particle in each of the second and third simulations is found by the (conversion equation m). The mass in the second simulation becomes $17.9 \times 10^{-26}$ [kg] which is obtained by multiplying the mass in the first simulation by $2^2$ (=4), and the mass in the third simulation becomes $71.7 \times 10^{-26}$ [kg] which is obtained by multiplying the mass in the first simulation by $4^2$ (=16).

Next, the initial arrangement of particles will be described. In the initial state, the particles are arranged on the lattice points of a face-centered cubic lattice. In the first simulation, 40 layers, in each of which 20 particles are arranged in a width direction and 20 particles are arranged in a depth direction, are arranged to overlap each other. A portion of $1/\alpha$ in the width direction, $1/\alpha$ in the depth direction, and $1/\alpha$ in the height direction of the original system (a portion of $1/\alpha^3$ of the original system) corresponds to the renormalized system. In the second simulation, 20 layers in each of which 10 particles are arranged in the width direction and 10 particles are arranged in the depth direction are arranged to overlap each other. In the third simulation, 10 layers in each of which 5 particles are arranged in the width direction and 5 particles are arranged in the depth direction are arranged to overlap each other.

Next, a time width of numerical integration will be described. It is assumed that a time width in the original system is $\Delta t$, and the velocity of the particle is v. The time width $\Delta t$ is determined, for example, so as to satisfy the following equation ("<<" means that the left side of the equation is sufficiently smaller than the right side).

$$\frac{v\Delta t}{r_0} \ll 1 \tag{5}$$

Here, $r_0$ is a constant in the inter-particle potential, and gives an indication of the inter-particle distance. It is assumed that a time width in the renormalized system is $\Delta t'$, and the velocity of the particle is $v'$. From the (conversion equation v), since $v'=v/\alpha$, the time width $\Delta t'$ in the renormalized system is set to, for example, $\alpha \Delta t$.

The time width of numerical integration was set to 5.0 [fs] in the first simulation, 10 [fs] in the second simulation, and 20 [fs] in the third simulation.

Next, an initial velocity which is given to a particle will be described. First, the relationship between the temperature of the original system and the temperature of the renormalized system will be described. The temperature T of the original system is defined by the following equation.

$$\frac{3}{2}k_B T = \frac{1}{N-1}\sum_i^N \frac{1}{2}m(v_i - v_g)^2 \tag{29}$$

Here, $k_B$ is the Boltzmann constant, $v_i$ is the velocity vector of a particle i, and $v_g$ is the velocity vector of the center of gravity of the particle system. The temperature is, that is, the "fluctuation" of the velocity. The temperature T' of the renormalized system is defined by the following equation.

$$\frac{3}{2}k_B T' = \frac{1}{N'-1}\sum_i^{N'} \frac{1}{2}m'(v_i' - v_g')^2 \tag{30}$$

In the original system, the kinetic energy of a particle having a mass m and a velocity v is $\frac{1}{2}mv^2$. In the renormalized system, the kinetic energy of a particle having a mass m' and a velocity v' is $\frac{1}{2}m'v'^2$. From the (conversion equation m) and the (conversion equation v), the following relationship is obtained.

$$\frac{1}{2}mv^2 = \frac{1}{2}\frac{m}{\alpha^2}(v\alpha)^2 = \frac{1}{2}m'v'^2 \tag{31}$$

Thus, the temperature T of the original system becomes equal to the temperature T' of the renormalized system. In the first to third simulations, the initial velocity is given such that the temperature of the particle system is at 300 [K].

Next, a method which flows heat into the particle system will be described. In the first to third simulations, the kinetic energy was given to particles arranged at the bottom of the particle system, and the inflow of heat into the system was simulated. A surface into which heats flows is called a heated surface.

First, a heat inflow method in the first simulation (that is, a heat inflow method in the original system) will be described. It is assumed that kinetic energy $\Delta E$ is given per particle on the heated surface with a time width $\Delta t$. A variation in the momentum vector of the particle is obtained by the following equation (32). Here, the momentum vector at a certain time t is $p_t$, and the momentum vector at a time $t+\Delta t$ is $P_{t+\Delta t}$.

$$\frac{p_t^2}{2m} - \frac{p_{t+\Delta t}^2}{2m} = \Delta E \tag{32}$$

It is assumed that the momentum vector becomes $\lambda$ times because of the kinetic energy $\Delta E$. That is, the following equation is assumed.

$$p_{t+\Delta t} = \lambda p_t \tag{33}$$

If the equation (33) is substituted in the equation (32), $\lambda$ is expressed as follows.

$$\lambda = \sqrt{1 + \frac{2m\Delta E}{p_t^2}} \tag{34}$$

The momentum vector is updated by the equation (33) for every time width $\Delta t$. Thus, the inflow of heat can be simulated such that the kinetic energy $\Delta E$ flows per time width $\Delta t$.

If the number of particles on the heated surface is $N_h$, and the area of the heated surface is $S_h$, power $f_h$ which flows per unit area is expressed as follows.

$$f_h = \frac{N_h \Delta E}{S_h \Delta t} \tag{35}$$

In the first simulation, the number $N_h$ of particles on the heated surface is 400, the area $S_h$ of the heated surface is $2.83\times10^{-17}$ [m$^2$], the kinetic energy $\Delta E$ is $4.14\times10^{-24}$ [J], the time width $\Delta t$ is 5.0 [fs], and the power $f_h$ is $1.17\times10^{10}$ [W/m$^2$].

In the second and third simulations (in the renormalized system), power $f_h'$ which flows per unit area is given by the following equation.

$$f_h' = f_h/\alpha \tag{36}$$

The coefficient $\lambda'$ for updating the momentum vector is given by the following equation.

$$\lambda' = \sqrt{1 + \frac{2m'\Delta E}{p_t'^2}} \tag{37}$$

From the equation (31), the kinetic energy $\Delta E$ to be given becomes equal between the original system and the renormalized system.

Figure 2:
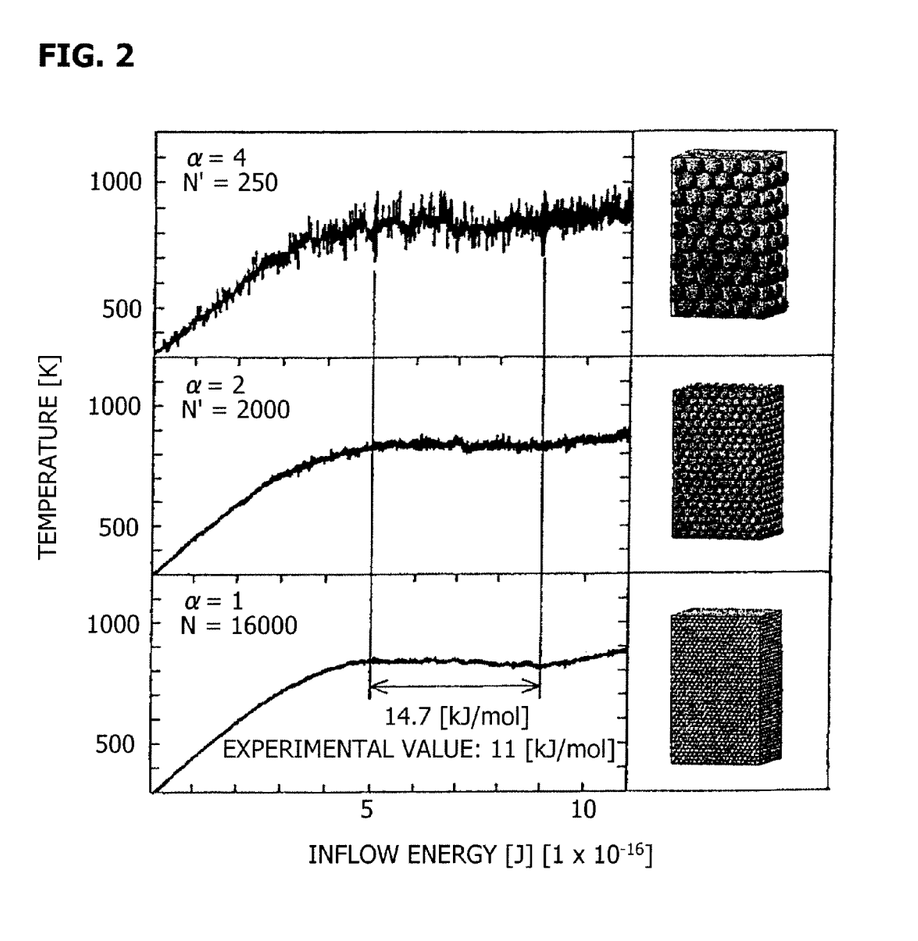
FIG. 2 is a graph showing a simulation result on aluminum using renormalization group molecular dynamics.

Next, simulation results will be described with reference to FIG. 2. Of the graphs shown in FIG. 2, a lower graph shows the result of the first simulation (molecular dynamics calculation of the related art), a middle graph shows the result of the second simulation (renormalization group molecular dynamics calculation when the renormalization factor $\alpha$ is 2), and an upper graph shows the result of the third simulation (renormalization group molecular dynamics calculation when the renormalization factor $\alpha$ is 4). In the three graphs, the vertical axis represents temperature (unit [K]), and the horizontal axis represents the amount of inflow heat, that is, inflow energy (unit $10^{-16}$ [J]).

First, the result of the first simulation will be described with reference to the lower graph. When no energy flows into the system, the temperature of the system is 300 [K]. As the inflow energy increases, the temperature of the system rises. If the inflow energy reaches about $5\times10^{-16}$ [J], temperature rise temporarily stops at about 850 [K], and the temperature is substantially constant until the inflow energy reaches about $9\times10^{-16}$ [J]. This temperature represents a melting point. If the inflow energy exceeds about $9\times10^{-16}$ [J], the temperature rises again.

Energy which flows into the system during a period in which the temperature is constant corresponds to latent heat. Latent heat which is obtained from this simulation becomes 14.7 [kJ/mol]. The melting point of aluminum experimentally obtained is 933 [K], and latent heat is 11 [kJ/mol]. It is considered that the difference between the value obtained by the simulation and an experimental value is due to the precision of the used inter-atom potential or the like.

Next, the results of the second and third embodiments will be described with reference to the middle and upper graphs. The results of the second and third simulations have the same tendency as the result of the first simulation. That is, there is a tendency that the temperature is substantially constant around at 850 [K] during a period in which the inflow energy is about $5\times10^{-16}$ [J] to about $9\times10^{-16}$ [J]. Thus, from the second and third simulations, it can be obtained that the melting point is about 850 [K], and latent heat is 14.7 [kJ/mol].

The energy which flows into the particle system is obtained by integrating the inflow power by the period in which the simulation is done. If the energy which flows into the renormalized system is E', the energy E which flows into the original system is obtained by the following equation.

$$E = \alpha^3 E' \tag{38}$$

The inflow energy per particle is equal between the original system and the renormalized system.

The temperature of the renormalized system is obtained from the equation (30). From the above discussion, the temperature of the original system is equal to the temperature of the renormalized system.

Although in the above-described simulation, the inflow energy and temperature in the original system are obtained, if necessary, other physical quantities in the original system, for example, the position, momentum, velocity, and the like of the particle can be obtained on the basis of the above-described scale conversion rule.

As described above, in renormalization group molecular dynamics, the physical quantities (in the above-described example, the melting point and latent heat) which are expected to be obtained by molecular dynamics calculation on a system before renormalization (the system corresponding to the first simulation in the above-described example) can be calculated by carrying out molecular dynamics calculation on a system having a smaller number of particles than the system before renormalization. Various kinds of calculation necessary for a simulation by renormalization group molecular dynamics can be carried out on a computer on the basis of a program.

In the simulation of the example, aluminum has a face-centered cubic lattice. Although the scale conversion rule is derived from the consideration on a particle system arranged on a simple cubit lattice, the invention is not limited to a simple cubic structure and is effectively applied to other crystal structures.

Next, a simulation in which heat flows into silicon to raise the temperature, and a melting point and latent heat are derived will be described. Silicon has a diamond structure. Similarly to the simulation of aluminum, three simulations were carried out. A first simulation is a molecular dynamics method of the related art for comparison. In second and third simulations, molecular dynamics calculation was carried out on a system renormalized from the system corresponding to the first simulation. The renormalization factor α was set to 2 in the second simulation and $2^2$ (=4) in the third simulation. The number of particles is 8192 in the first simulation, 1024 in the second simulation, and 128 in the third simulation.

As the inter-atom potential in the first simulation (that is, the inter-particle potential in the original system), the S-W (Stillinger-Weber) potential was used. This potential is expressed.

$$\phi = \sum_{i<j} \varepsilon f(r_{ij}/\sigma) + \sum_{i<j<k} \varepsilon g(r_i/\sigma, r_j/\sigma, r_k/\sigma) \tag{39}$$

Here, the definition is made as follows.

$f(x) = A(B/x^p - 1/x^q)\exp\{1/(x-a)\}$ $(x<a)$ $f(x) = 0$ $(x>a)$ $g(x_i,x_j,x_k) = h(x_{ij},x_{ik},\theta_{ijk}) + h(x_{ji},x_{jk},\theta_{jik}) + h(x_{ki},x_{kj},\theta_{kij})$ $h(x_{ij},x_{ik},\theta_{ijk}) = \lambda \exp\{\gamma/(x_{ij}-a) + \gamma/(x_{ik}-a)\}(\cos\theta_{ijk} + \frac{1}{3})^2$
$(x_{ij}<a, x_{ik}<a)$ $h(x_{ij},x_{ik},\theta_{ijk}) = 0$ $(x_{ij}>a, x_{ik}>a)$ The interaction coefficient ε is 2.167 [eV], σ is 2.095 [Å], the constants A, B, p, q, a, λ, and γ are respectively 7.05, 0.602, 4.0, 0.0, 1.8, 21.0, and 1.2.

Figure 3A:
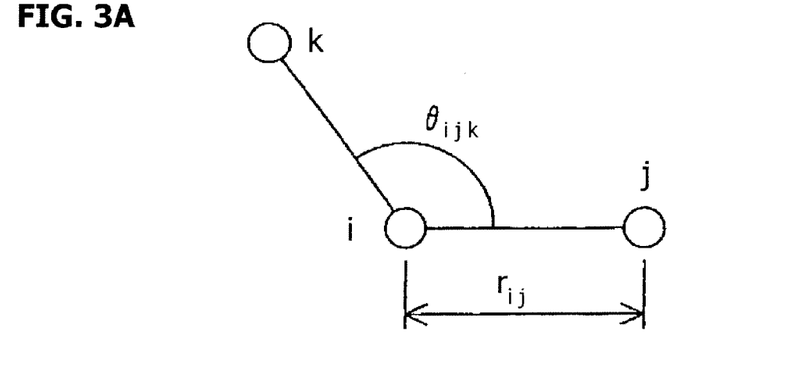
FIG. 3A is a diagram illustrating an S-W potential.

As shown in FIG. 3A, the angle of coupling between particles i and k and coupling between particles i and j is $\theta_{ijk}$, and the inter-particle distance from the particle i to the particle j is $r_{ij}$. The renormalized interaction coefficient in the inter-particle potential of each of the second and third simulations is obtained by the same method as in the simulation of aluminum.

The mass of a silicon atom in the first simulation (that is, the mass of a particle in the original system) was set to $4.67\times10^{-26}$ [kg]. The renormalized mass in each of the second and third simulations is obtained by the same method as in the simulation of aluminum.

Figure 3B:
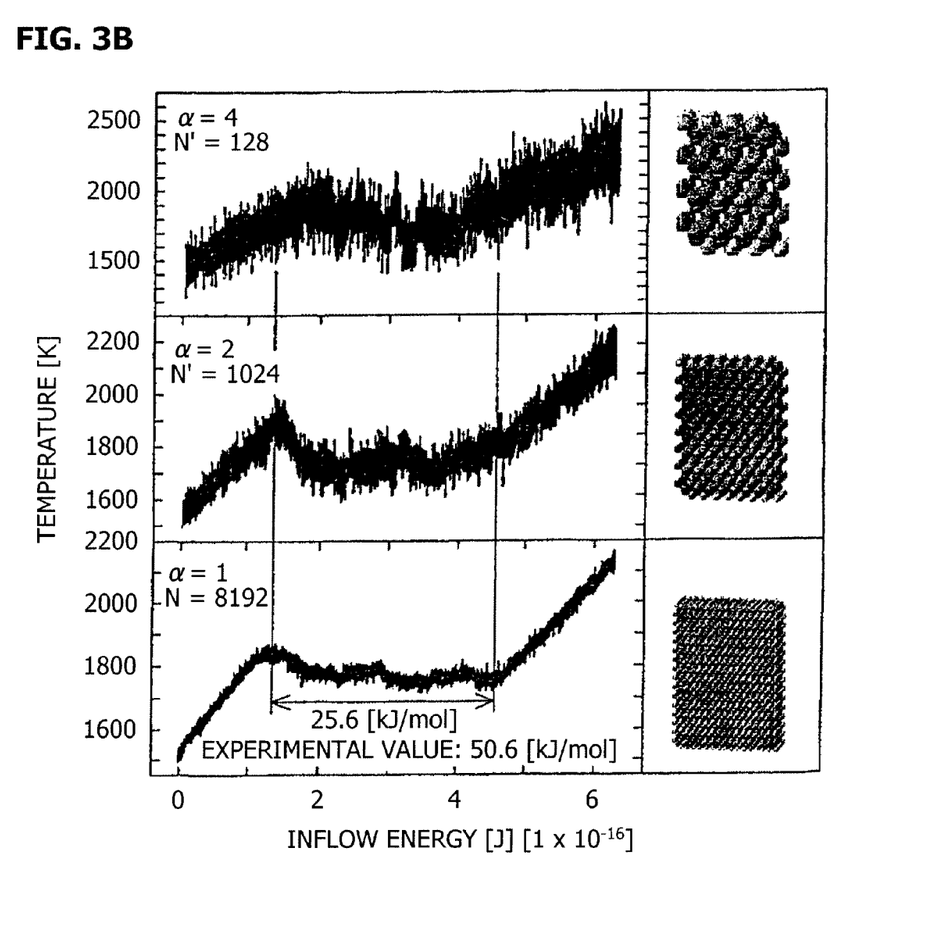
FIG. 3B is a graph showing a simulation result on silicon using renormalization group molecular dynamics.

Next, simulation results will be described with reference to FIG. 3B. Of the graphs shown in FIG. 3B, a lower graph shows the result of the first simulation (molecular dynamics calculation of the related art), a middle graphs shows the result of the second simulation (renormalization group molecular dynamics calculation when the renormalization factor α is 2), and an upper graph shows the result of the third simulation (renormalization group molecular dynamics calculation when the renormalization factor α is 4).

First, the result of the first simulation will be described with reference to the lower graph. During a period in which the inflow energy increases from about $1.3\times10^{-16}$ [J] to about $4.6\times10^{-16}$ [J], the temperature is substantially constant at about 1750 [K]. Latent heat is obtained to be 25.6 [kJ/mol]. The melting point of silicon experimentally obtained is 1687 [K], and latent heat is 50.6 [kJ/mol]. It is considered that the difference between the value obtained in the simulation and the experimental value is due to the precision of the inter-atom potential or the like.

Next, the results of the second and third simulations will be described with reference to the middle and upper graphs. The results of the second and third simulations substantially have the same tendency as the result of the first simulation. Thus, the melting point and latent heat close to the values obtained in the first simulation can be obtained on the basis of the second and third simulations.

Figure 4:
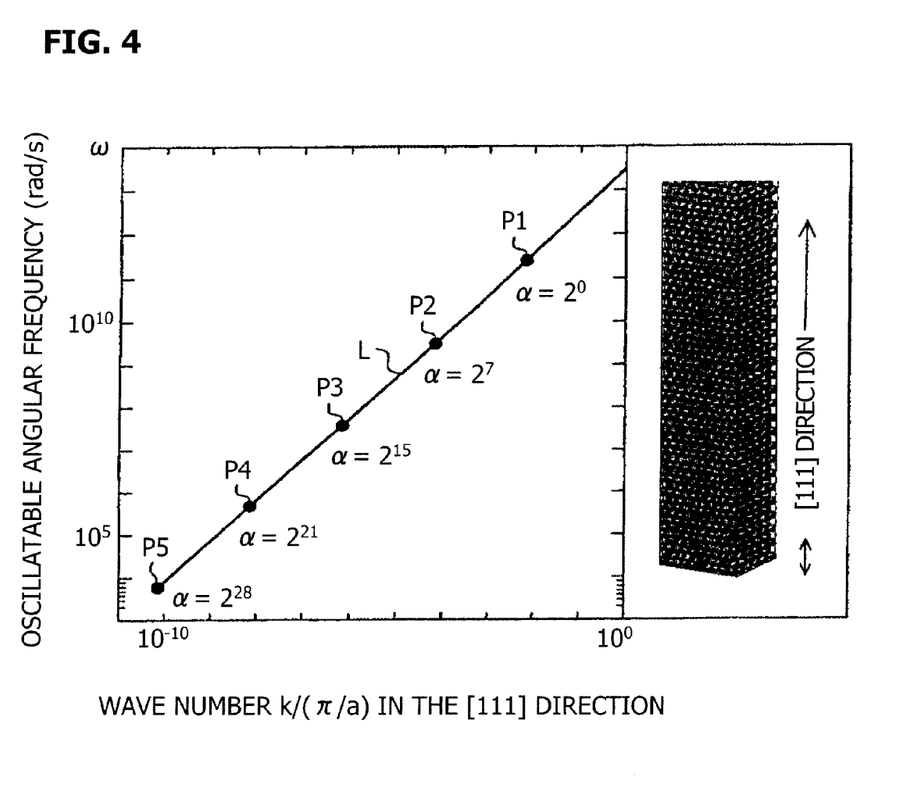
FIG. 4 is a graph showing a simulation result when a dispersion relationship is obtained using renormalization group molecular dynamics.

Next, a simulation in which a dispersion relationship is obtained by renormalization group molecular dynamics will be described with reference to FIG. 4. Vibration was applied in parallel to the [111] direction of aluminum to calculate the wave number in the [111] direction. The atoms were connected to each other through springs. A spring constant s was set to 40.3 [N/m]. The spring constant s is obtained by approximating the near-minimum value of the inter-atom potential of aluminum using a quadratic function. The mass m of an aluminum atom was set to $4.48 \times 10^{-26}$ [kg]. The inter-atom distance a was set to the $2.86 \times 10^{-10}$ [m]. The exact solution (the solution analytically obtained) of the dispersion relationship is given by the following equation when an oscillatable angular frequency is $\omega$ and the wave number in the [111] direction is k.

$$\omega = \left(\frac{4s}{m}\right)^{1/2} \sin\left(\frac{ka}{2}\right)$$

The exact solution can be obtained by $\alpha=1$ in the equation (26). A solid line L in the graph indicates an exact solution. A point P1 indicates the result of molecular dynamics calculation of the related art (corresponding to when the renormalization factor $\alpha=1$). Points P2 to P5 respectively indicate the results when the renormalization factor $\alpha$ is $2^7$, $2^{15}$, $2^{21}$, and $2^{28}$. The point that the renormalization factor $\alpha$ increases means that the size of the original system (the system before renormalization) increases. The renormalization factor $\alpha$ increases, obtaining a small wave number. The result obtained by renormalization group molecular dynamics satisfactorily coincides with an exact solution. In this way, if renormalization group molecular dynamics is used, calculation in a long wavelength region which is not easily carried out in molecular dynamics of the related art (calculation on a macro system which is regarded as a continuous body) can be carried out with good precision.

An XYZ orthogonal coordinate system is considered in a space where a particle system is arranged. In the above-described example, the renormalized position vector q' was obtained from the position vector q of the original system on the basis of the renormalization factor $\alpha$.

$q'=q/\alpha$ (conversion equation q)

This indicates that spatial scale conversion in all the X, Y, and Z directions is carried out by the common renormalization factor $\alpha$. The renormalization factor $\alpha$ can be set separately in each of the X, Y, and Z directions. That is, scale conversion having anisotropy may be carried out.

When the second renormalization factor $\gamma$ is determined to be 0 and the third renormalization factor $\alpha$ is determined to be 2, a scale conversion rule having anisotropy is expressed by the following conversion equation. The renormalization factor in the X direction is $\alpha_X$, the renormalization factor in the Y direction is $\alpha_Y$, and the renormalization factor in the Z direction is $\alpha_Z$. Each of the renormalization factors $\alpha_X$ to $\alpha_Z$ is, for example, $2^n$ (where n is a positive integer).

The number N of particles of the particle system S and the number N' of renormalized particles of the renormalized particle system S' are associated with each other by the following conversion equation.

$N'=N/\alpha_X\alpha_Y\alpha_Z$ (conversion equation Na)

Each component of the position vector q of a certain particle of the particle system S and each component of the position vector q' of a certain particle of the renormalized particle system S' are associated with each other by the following conversion equation.

$q'_\eta=q_\eta/\alpha_\eta$ (conversion equation qa)

Here, $\eta$ represents one of the X, Y, and Z components of a vector (hereinafter, the same is applied to (conversion equation pa), (conversion equation va), and (conversion equation ma)). Each component of the momentum vector p of a certain of the particle system S and each component of the momentum vector p' of a certain particle of the renormalized particle system S' are associated with each other by the following conversion equation.

$p_\eta'=p_\eta\alpha_\eta$ (conversion equation pa)

When $\gamma=0$ and $\delta$ is undetermined, $\delta$ is determined, and the following equation is substituted, such that association is made.

$p_\eta'=p_\eta\alpha_\eta^{\delta/2}$

Each component of the velocity vector v of a certain particle of the particle system S and each component of the velocity vector v' of a certain particle of the renormalized particle system S are associated with each other by the following conversion equation.

$v_\eta'=v_\eta/\alpha_\eta$ (conversion equation va)

When $\gamma=0$ and $\delta$ is undetermined, $\delta$ is determined, and the following equation is substituted, such that association is made.

$v_\eta'=v_\eta/\alpha_\eta^{\delta/2}$

Since the renormalization factor in each direction is set, the mass of the particle is subjected to scale conversion in each direction. The mass m of each particle of the particle system S and the mass $m'_X$ in the X direction, the mass $m'_Y$ in the Y direction, and the mass $m'_Z$ in the Z direction of each particle of the renormalized particle system S' are associated with each other by the following conversion equation.

$m_\eta'=m\alpha_\eta^2$ (conversion equation ma)

The corresponding mass is used by each direction in the equation (25) of motion in the renormalized system.

When $\gamma=0$ and $\delta$ is undetermined, $\delta$ is determined, and the following equation is substituted, such that association is made.

$m_\eta'=m\alpha_\eta^\delta$

The interaction coefficient $\epsilon$ in the particle system S and the interaction coefficient $\epsilon'$ in the renormalized particle system S' are associated with each other by the following conversion equation.

$\epsilon'=\epsilon$ (conversion equation $\epsilon$a)

The time scale t in the particle system S and the scale t' in the renormalized particle system S are associated with each other by the following conversion equation.

$t'=t$ (conversion equation ta)

For example, a simulation of a thin film is considered. A thin film has a larger film thickness in a direction parallel to the film surface than in a film thickness direction. Thus, the renormalization factor is greater in the direction parallel to the film surface than in the film thickness direction. For example, if the film thickness direction is the Z direction, it should suffice that the renormalization factors $\alpha_X$ and $\alpha_Y$ in the direction parallel to the film surface are set to be greater than the renormalization factor $\alpha_Z$ in the film thickness direction.

The second scaling parameter $\gamma$ is included in the (conversion equation m), the (conversion equation $\epsilon$), and the (conversion equation t) in the form of $\alpha^\gamma$. When $\gamma=0$ is set, $\alpha^\gamma$ simply becomes "1". Thus, for example, when it is determined to be $\delta=2$, with regard to the mass of the particle, the interaction coefficient, and the time, the following scale conversion may be carried out without using the second scaling parameter $\gamma$ (without introducing a second scaling parameter as $\gamma$).

$$m'=m\alpha^2$$

$$\epsilon'=\epsilon$$

$$t'=t$$

In this case, the same scale conversion as when the second scaling parameter $\gamma$ is set to 0 is carried out. When $\gamma=0$ and $\delta=2$, with regard to the velocity vector, the following scale conversion is carried out.

$$v'=v/\alpha$$

If the renormalization factors $\alpha$, $\alpha_X$, $\alpha_Y$, and $\alpha_Z$ are greater than 1, the number of particles in the renormalized system is smaller than the number of particles in the original system.

If necessary, the renormalization factor (for example, $\alpha$) may differ between a certain portion and another portion of a system which will be subjected to a simulation.

In the above-described example, as the example of renormalization group molecular dynamics, the melting point, latent heat, and the dispersion relationship have been obtained. Renormalization group molecular dynamics is not limited thereto and may be used for the simulations of various kinds of physical phenomenon. Renormalization group molecular dynamics uses molecular dynamics and can be thus applied to various problems which are handled in molecular dynamics. For example, problems of flow, structure, heat, reaction, and the like, problems of mechanism, abrasion, and lubrication, and the like can be handled. With renormalization group molecular dynamics, it is possible to obtain the physical quantities of a system having a larger number of particles than a system in which molecular dynamics calculation is actually carried out. Thus, if renormalization group molecular dynamics which has been found by the inventors is used, it becomes possible to carry out a precise simulation on a problem of scaling on which a simulation is not easily carried out in the related art. As the method of molecular dynamics calculation which is executed in renormalization group molecular dynamics, various known methods may be used.

In NPL 1 described in the "DESCRIPTION OF THE RELATED ART" of this specification, there is an attempt to apply the renormalization technique to molecular dynamics. However, in NPL 1, only the interaction portion of the Hamiltonian is renormalized, and the kinetic energy portion is not renormalized. In NPL 1, with regard to the momentum (or velocity), simple average, not renormalization, is taken. For this reason, static analysis is still done, a temperature may not be taken into consideration explicitly, and an artificial method (the equations (23), (24), and (25) described in "3. Numerical Calculation Method" of NPL 1) is necessary for forcibly causing energy dissipation. For this reason, at the time of the application to calculation of finite temperature or dynamic problems involved in vibration, noise, and phase transition, there is a problem in that reliability is lacking. The scale conversion rule described in NPL 1 corresponds to a case when $\gamma=0$ and $\delta=3$ in the invention.

In the course of deriving the scale conversion rule of the inventors, the kinetic energy portion of the Hamiltonian is renormalized. Thus, an appropriate scale conversion rule of the momentum vector (or velocity vector) is derived. Therefore, it becomes possible to take into consideration a temperature explicitly in a simulation.

Although the invention has been described in connection with the example, the invention is not limited to the example. For example, it is obvious to those skilled in the art that various changes, improvements, combinations, or the like may be made.

What are claimed are:

1. A simulation method comprising the steps of:
   (a) determining, via a processor, a first renormalization factor $\alpha$ greater than 1, a second renormalization factor $\gamma$ equal to or greater than 0 and equal to or smaller than d, and a third renormalization factor $\delta$ equal to or greater than 0 using a dimension number d of a space where a particle system S is arranged to obtain a number N' of renormalized particles by a conversion equation $N'=N/\alpha^d$, to obtain a mass m' of each renormalized particle by a conversion equation $m'=m\alpha^\delta/\alpha^\gamma$, and to obtain a renormalized interaction coefficient $\epsilon'$ by a conversion equation $\epsilon'=\epsilon\alpha^\gamma$, wherein the particle system S in which a number of particles is N, a mass of each particle is m, and inter-particle interaction potential energy can be expressed by a product $\epsilon f$ of a dimensionless function f representing an inter-particle distance dependence and an interaction coefficient $\epsilon$; and
   (b) performing, via the processor, a molecular dynamics calculation on a renormalized particle system S' in which the number of renormalized particles is N', the mass of each particle is the mass m' of each renormalized particle, and inter-particle interaction potential energy is expressed by a product $\epsilon'f$ of the dimensionless function f and the renormalized interaction coefficient $\epsilon'$.

2. The simulation method according to claim 1, further comprising the step of:
   (c) when the position vector of a certain particle in the renormalized particle system S' obtained by molecular dynamics calculation in the step (b) is q', the momentum vector of a certain particle in the renormalized particle system S' obtained by molecular dynamics calculation in the step (b) is p', the velocity vector of a certain particle in the renormalized particle system S' obtained by molecular dynamics calculation in the step (b) is v', and a certain time interval of a certain particle in the renormalized particle system S' during molecular dynamics calculation in the step (b) is t', carrying out at least one of calculation for obtaining the position vector q of a certain particle in the particle system S by a conversion equation $q=q'\alpha$, calculation for obtaining the momentum vector p of a certain particle in the particle system S by a conversion equation $p=p'/\alpha^{\delta/2}$, calculation for obtaining the velocity vector v of a certain particle in the particle system S by a conversion equation $v=v'\alpha^{(-\gamma+\delta/2)}$, and calculation for obtaining a certain time interval t during molecular dynamics calculation assumed to be carried out on the particle system S by a conversion equation $t=t'\alpha^{(1+\gamma-\delta/2)}$ using at least one of the first renormalization factor $\alpha$, the second renormalization factor $\gamma$, and the third renormalization factor $\delta$ determined in the step (a).

3. The simulation method according to claim 1, wherein the second renormalization factor $\gamma$ is 0.

4. The simulation method according to claim 1, wherein the first renormalization factor is $2^n$ where n is a positive integer.

5. The simulation method according to claim 1, wherein the dimension number d is 3.

6. A simulation method comprising the steps of:
(a) determining, via a processor, a first renormalization factor a greater than 1 and a third renormalization factor δ equal to or greater than 0 using a dimension number d of a space where a particle system S is arranged to obtain the number N' of renormalized particles by conversion equation $N'=N/\alpha^d$ and to obtain the mass m' of each renormalized particle by a conversion equation $m'=m\alpha^\delta$, wherein the particle system S in which a number of particles is N, a mass of each particle is m and inter-particle interaction potential energy can be expressed by a product ϵf of a dimensionless function f representing inter-particle distance dependence and an interaction coefficient ϵ; and
(b) performing, via the processor, a molecular dynamics calculation on a renormalized particle system S' in which the number of renormalized particles is N', the mass of each particle is the mass m' of each renormalized particle, and inter-particle interaction potential energy is expressed by the product ϵf of the dimensionless function f and the interaction coefficient ϵ.

7. The simulation method according to claim 6, further comprising the step of:
(c) when the position vector of a certain particle in the renormalized particle system S' obtained by molecular dynamics calculation in the step (b) is q', the momentum vector of a certain particle in the renormalized particle system S' obtained by molecular dynamics calculation in the step (b) is p', and the velocity vector of a certain particle in the renormalized particle system S' obtained by molecular dynamics calculation in the step (b) is v', carrying out at least one of calculation for obtaining the position vector q of a certain particle in the particle system S by a conversion equation $q=q'\alpha$, calculation for obtaining the momentum vector p of a certain particle in the particle system S by a conversion equation $p=p'/\alpha^{\delta/2}$, and calculation for obtaining the velocity vector v of a certain particle in the particle system S by a conversion equation $v=v'\alpha^{\delta/2}$ using at least one of the first renormalization factor a and the third renormalization factor δ determined in the step (a).

8. A simulation method comprising the steps of:
(d) obtaining, via a processor, a number N' of renormalized particles by a conversion equation $N'=N/(\alpha_x\alpha_y\alpha_z)$, and further determining a renormalization factor δ equal to or greater than 0 to obtain a mass $m_x'$ of each renormalized particle regarding an X direction by a conversion equation $m_x'=m\alpha_x^\delta$, to obtain a mass $m_y'$ of each renormalized particle regarding a Y direction by a conversion equation $m_y'=m\alpha_y^\delta$, and to obtain a mass $m_z'$ of each renormalized particle regarding a Z direction by a conversion equation $m_z'=m\alpha_z^\delta$, wherein a particle system S in which a number of particles is N, a mass of each particle is m, and inter-particle interaction potential energy can be expressed by a product ϵf of a dimensionless function f representing inter-particle distance dependence and an interaction coefficient ϵ, and an XYZ orthogonal coordinate system in a space where the particle system S is arranged, on the basis of a renormalization factor $\alpha_x$ in an X direction, a renormalization factor $\alpha_y$ in a Y direction, and a renormalization factor $\alpha_z$ in a Z direction greater than 1; and
(e) performing, via the processor, a molecular dynamics calculation on a renormalized particle system S', in which the number of renormalized particles is N', the mass of each particle is a mass m' of each renormalized particle, and inter-particle interaction potential energy is expressed by the product ϵf of the dimensionless function f and an interaction coefficient ϵ, using the mass $m_x'$ of each renormalized particle regarding the X direction for an equation of motion in the X direction, the mass $m_y'$ of each renormalized particle regarding the Y direction for an equation of motion in the Y direction, and the mass $m_z'$ of each renormalized particle regarding the Z direction for an equation of motion in the Z direction.

9. The simulation method according to claim 8, further comprising the step of:
(f) when the position vector of a certain particle in the renormalized particle system S' obtained by molecular dynamics calculation in the step (e) is q', the components in the X, Y, and Z directions of the position vector q' are respectively $q_x'$, $q_y'$, and $q_z'$, the momentum vector of a certain particle in renormalized the particle system S' obtained by molecular dynamics calculation in the step (e) is p', the components in the X, Y, and Z directions of the momentum vector p' are respectively $p_x'$, $p_y'$, and $p_z'$, the velocity vector of a certain particle in the renormalized particle system S' obtained by molecular dynamics calculation in the step (e) is v', and the components in the X, Y, and Z directions of the velocity vector v' are respectively $v_x'$, $v_y'$, and $v_z'$, carrying out at least one of calculation for respectively obtaining the components $q_x$, $q_y$, and $q_z$ in the X, Y, and Z directions of the position vector q of a certain particle in the particle system S by conversion equations $q_x=q_x'\alpha_x$, $q_y=q_y'\alpha_y$, and $q_z=q_z'\alpha_z$, calculation for respectively obtaining the components $p_x$, $p_y$, and $p_z$ in the X, Y, and Z directions of the momentum vector p of a certain particle in the particle system S by conversion equations $p_x=p_x'/\alpha_x^{\delta/2}$, $p_y=p_y'/\alpha_y^{\delta/2}$, and $p_z=p_z'/\alpha_z^{\delta/2}$, and calculation for respectively obtaining the components $v_x$, $v_y$, and $v_z$ in the X, Y, and Z directions of the velocity vector v of a certain particle in the particle system S by conversion equations $v_x=v_x'\alpha_x^{\delta/2}$, $v_y=v_y'\alpha_y^{\delta/2}$, and $v_z=v_z'\alpha_z^{\delta/2}$ using the renormalization factor $\alpha_x$ in the X direction, the renormalization factor $\alpha_y$ in the Y direction, the renormalization factor $\alpha_z$ in the Z direction, and the renormalization factor ϵ determined in the step (d).

10. The simulation method according to claim 8, wherein at least two of the renormalization factor $\alpha_x$ in the X direction, the renormalization factor $\alpha_y$ in the Y direction, and the renormalization factor $\alpha_z$ in the Z direction are different from each other.

* * * * *